US012533266B2

(12) United States Patent
Wroe Neild et al.

(10) Patent No.: US 12,533,266 B2
(45) Date of Patent: Jan. 27, 2026

(54) KIT FOR USE WITH A SELECTIVELY CONFIGURABLE WOUND DRESSING

(71) Applicant: ConvaTec Limited, Deeside (GB)

(72) Inventors: Sarah Wroe Neild, Deeside (GB); Manjunath Penagondla, Deeside (GB); Natalie Brown, Deeside (GB); Chandan Rangaiah, Deeside (GB); Liam Davies, Deeside (GB)

(73) Assignee: CONVATEC LIMITED, Flintshire (GB)

( * ) Notice: Subject to any disclaimer, the term of this patent is extended or adjusted under 35 U.S.C. 154(b) by 451 days.

(21) Appl. No.: 17/871,682

(22) Filed: Jul. 22, 2022

(65) Prior Publication Data

US 2023/0023971 A1 Jan. 26, 2023

Related U.S. Application Data

(63) Continuation of application No. PCT/GB2022/051920, filed on Jul. 22, 2022.

(30) Foreign Application Priority Data

Jul. 23, 2021 (GB) .................................... 2110651

(51) Int. Cl.

*A61F 13/0203* (2024.01)
*A61F 13/00* (2024.01)
*A61F 13/0206* (2024.01)

(52) U.S. Cl.

CPC ...... *A61F 13/0223* (2013.01); *A61F 13/0206* (2013.01); *A61F 2013/00174* (2013.01)

(58) Field of Classification Search

CPC .............. A61F 13/0223; A61F 13/0206; A61F 2013/00174; B26F 1/38; B26F 1/3846;

(Continued)

(56) References Cited

U.S. PATENT DOCUMENTS 5,860,217 A * 1/1999 Braun ..................... B26B 29/06 30/310
2009/0048635 A1* 2/2009 Andino ................ A61N 1/0468 607/2

(Continued)

FOREIGN PATENT DOCUMENTS

EP 2604299 A1 6/2013
EP 4251110 A1 10/2023

(Continued)

OTHER PUBLICATIONS

UKIPO Search Report of corresponding application GB2110651.3; Date: Apr. 28, 2022; pp. 2.

*Primary Examiner* — Jessica Arble
(74) *Attorney, Agent, or Firm* — TAFT STETTINIUS HOLLISTER LLP; Ryan O. White; Derek B. Lavender

(57) ABSTRACT

Kit for use with A Selectively Configurable Wound Dressing A packaged kit of parts is provided for use with a selectively configurable wound dressing. The kit includes a piercing tool configured to pierce a covering layer of the wound dressing to produce an aperture therein and thereby configure the wound dressing for use in a pressure gradient wound therapy system. The kit may also include a) packaging indicating that the piercing tool is configured to pierce a covering layer of a wound dressing; (b) instructions instructing a user as to how to use the piecing tool; (c) one or more selectively configurable wound dressings; (d) a source of non-atmospheric pressure; (e) a port to connect the wound dressing to a source of non-atmospheric pressure; or (f) tubing for connection between a wound dressing and a source of non-atmospheric pressure. The kit is arranged within a sealed package.

23 Claims, 7 Drawing Sheets

(58) Field of Classification Search
CPC ...... B26F 1/36; B26F 1/14; B26F 1/32; B26F 1/405; B26F 1/44; B26F 2001/4481
See application file for complete search history.

(56) References Cited

U.S. PATENT DOCUMENTS

| | | | | |
|---|---|---|---|---|
| 2010/0106184 | A1* | 4/2010 | Coward | A61F 13/01034 606/213 |
| 2015/0159066 | A1* | 6/2015 | Hartwell | A61F 13/05 604/319 |
| 2015/0258259 | A1 | 9/2015 | Johannison | |
| 2018/0104394 | A1 | 4/2018 | Locke et al. | |
| 2018/0296395 | A1* | 10/2018 | Kubek | A61F 13/05 |
| 2018/0369462 | A1* | 12/2018 | Anderson | A61M 1/912 |
| 2020/0000985 | A1 | 1/2020 | Seddon et al. | |
| 2020/0023106 | A1 | 1/2020 | Carroll et al. | |
| 2020/0086016 | A1* | 3/2020 | Bannister | A61M 1/92 |
| 2020/0100945 | A1 | 4/2020 | Albert et al. | |
| 2020/0337906 | A1 | 10/2020 | Long et al. | |

FOREIGN PATENT DOCUMENTS

| | | | |
|---|---|---|---|
| WO | 2020051548 | A1 | 3/2020 |
| WO | 2020146154 | A2 | 7/2020 |

* cited by examiner

KIT FOR USE WITH A SELECTIVELY CONFIGURABLE WOUND DRESSING

CROSS REFERENCE TO RELATED DISCLOSURES

The present application is a continuation of International Application No. PCT/GB2022/051920 filed on Jul. 22, 2022 and claims the benefit of GB2110651.3 filed on Jul. 23, 2021, the contents of which are incorporated herein by reference in entirety.

TECHNICAL FIELD OF THE INVENTION

The present invention relates to kit for use with a wound dressing, in particular to a wound dressing selectively configurable for use in a pressure gradient wound therapy apparatus or for use without a pressure gradient wound therapy apparatus.

BACKGROUND TO THE INVENTION

Health care professionals (HCPs) are required to evaluate and treat a variety of wounds with different requirements which can change as treatment progresses. Accordingly, HCPs keep stocks of different types of dressings for different requirements.

Pressure gradient wound therapy (positive or negative) is one known way of treating various wound types. Typically, this involves applying a pressure differential between a sealed region of a wound dressing and the surrounding environment to assist with healing the wound, e.g. through removal of oedema, increasing blood flow, mechanical contraction of the wound, increasing formation of granulation tissue and/or active removal of excess exudate from the wound. Wound therapy of this type is particularly effective for the treatment of open traumatic, non-traumatic and chronic wounds.

Amongst different types of dressings are those designed and intended for use as an advanced wound dressing to manage exudate and protect the wound. These can, for example, have a wound contact layer including gelling fibres, such as the Hydrofiber (®™) technology included in Aquacel (®™) surgical dressings available from ConvaTec Ltd of Deeside, UK, which transform into a gel on contact with wound fluid. (Such wound dressings are not intended for use with pressure gradient wound therapy, nor used for such applications in practice, owing to their construction.)

Other types of wound dressing are specially adapted to be used in conjunction with a pressure gradient wound therapy apparatus, e.g. with a negative pressure wound therapy (NPWT pump). In their original incarnation, NWPT systems had large, heavy (not portable/wearable) pump arrangements connected via tubing to the wound; at the wound, a reticulated open cell foam dressing is introduced into the wound and a separate adhesive drape is placed over the top. To connect the tubing to the wound in these large systems, a health care professional pinches the drape and foam beneath, and snips a hole through both drape and foam to form an aperture in the top for connection to the tubing. These systems and the two-part wound dressing (i.e. separate foam and drape) are still widely used in hospitals where professional staff are on-hand to set up the systems.

More recently, and especially in portable or wearable pressure gradient wound therapy systems intended for home-use, one-piece dressings have been introduced, in which an adhesive covering layer and dressing are integrated. An example of such a dressing is the Avelle (®™) dressing available from ConvaTec Limited of Deeside UK. That dressing has a covering film layer with an adhesive border provided around its periphery to form a seal around the wound and a wound contact layer of stitch-bonded Hydrofiber (®™) material. A foam pressure-distribution layer is provided between the covering layer and the wound contact layer (adjacent the covering layer) and additional layers of fenestrated Hydrofiber (®™) layers are provided between the wound contact layer and the pressure-distribution layer. The covering layer is provided with an aperture, to allow connection of tubing from the negative pressure source and in this example, the dressing includes an "airway" extending from the aperture to a connector for connection to tubing through which negative pressure is provided.

Naturally, where a hospital or the like provides both "normal" wound dressings and those for use with pressure gradient wound therapy it needs to keep stocks of both, in various different sizes, which requires space, and lends complexity to the stock-ordering and stock selection process.

The present inventors have identified that it would be beneficial to be able to use a dressing for both pressure gradient wound therapy and "normal" treatment of wounds without a pressure gradient, in order that such treatment could be applied as and when required, and if no longer required, the dressings could still be used.

It is an aim of an embodiment or embodiments of the invention to overcome or at least partially mitigate one or more problems with the prior art and/or to provide an improved wound dressing.

SUMMARY OF THE INVENTION

According to a broad aspect of the invention there is provided a piercing tool configured to pierce a covering layer of a wound dressing to produce an aperture therein and thereby configure the wound dressing for use in a pressure gradient wound therapy system.

The piercing tool may be provided in a kit of parts. The kit may be for use with a selectively configurable wound dressing, the wound dressing being configurable for use in a pressure gradient wound therapy system and without a pressure gradient wound therapy system. The kit may be packaged. The kit may comprise at least one of: a) packaging indicating that the piercing tool is configured to pierce a covering layer of a wound dressing to produce an aperture therein and thereby configure the wound dressing for use in a pressure gradient wound therapy; (b) instructions instructing a user as to how to use the piecing tool to configure a wound dressing for use in a pressure gradient wound therapy system; (c) one or more selectively configurable wound dressings, the wound dressings being configurable for use in a pressure gradient wound therapy system and without a pressure gradient wound therapy system; (d) a source of non-atmospheric pressure; (e) a port for connection to the covering layer of the wound dressing to connect the wound dressing to a source of non-atmospheric pressure; or (f) tubing for connection between a wound dressing and a source of non-atmospheric pressure; the kit being arranged within a sealed package.

According to an aspect of the invention there is provided a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least one of: a) packaging indicating that the piercing tool is configured to pierce a covering layer of a wound dressing to produce an aperture therein and thereby configure the wound dressing for use in a pressure gradient wound therapy; (b) instructions instructing a user as to how to use the piecing tool to configure a wound dressing for use in a pressure gradient wound therapy system; (c) one or more selectively configurable wound dressings, the wound dressings being configurable for use in a pressure gradient wound therapy system and without a pressure gradient wound therapy system; (d) a source of non-atmospheric pressure; (e) a port for connection to the covering layer of the wound dressing to connect the wound dressing to a source of non-atmospheric pressure; or (f) tubing for connection between a wound dressing and a source of non-atmospheric pressure; the kit being arranged within a sealed package.

Advantageously providing a piercing tool configured to pierce a covering layer of the wound dressing to produce an aperture therein makes it possible to change the configuration of a wound dressing. Accordingly, a wound dressing which is normally sealed, e.g. by a closed, sealed and/or uninterrupted cover layer and thereby (only) suitable for use without a pressure gradient wound therapy system can be reconfigured, by introducing an aperture therein so as to configure the wound dressing for use in a pressure gradient wound therapy system (in which non-atmospheric pressure, e.g. negative pressure, can be applied through the aperture).

By allowing the reconfiguration of wound dressings, stock-keeping is simplified. Moreover, if, during "normal" treatment without pressure gradient it is determined that it would be beneficial for pressure gradient wound therapy to be used, such a system could be added, by configuring the wound dressing accordingly (i.e. cutting an aperture) and attaching a source of non-atmospheric pressure (e.g. tubing from a NWPT pump). Notably, this could be done without the need for an additional dressing change, thus reducing the risk of wound infection. Similarly, if a wound is being treated with a pressure gradient, e.g. NWPT and the amount of exudate produced is reduced, so that NWPT is no longer required, a patient would be able to use up the stock of dressings without the NWPT system, by configuring them for use without the system (i.e. by not cutting an aperture in them).

Providing a piercing tool along with one or more other items necessary to understand its function is also advantageous. For example, by including the packaging/instructions of (a) or (b)) a user can understand how to use the piercing tool in accordance with the invention; by including the dressings of (c) with which it is to be used, a user has all that is necessary to configure the dressings as desired; and by including one or more of the parts of a pressure gradient wound therapy apparatus, the user will have the piercing tool to hand when setting up the apparatus, ready to reconfigure dressings (which may of course have been obtained separately) for use with the pressure gradient wound therapy apparatus.

When used herein and throughout the specification the term "pressure gradient wound therapy apparatus" is intended to cover a wound therapy apparatus wherein a pressure differential (either positive or negative) is applied between a sealed region of the wound dressing and the surrounding environment.

As used herein, negative pressure wound therapy is a therapeutic technique using a suction dressing to remove excess exudation and promote healing in acute or chronic wounds. A vacuum of −50 to −200 mm Hg, or −75 to −150 mm Hg may be applied with typical negative pressure of −80 to −130 mm Hg, −100 to −130 mm Hg, or often about −125 mm Hg being applied to a wound.

For positive pressure wound therapy, a net positive pressure is applied to the wound, which may include providing simultaneous aspiration and irrigation of the wound. Positive pressure wound therapy may be carried out at a positive pressure of up to 50% atm., typically at a low positive pressure of up to 20% atm., more usually up to 10% atm. at the wound. Positive pressure wound therapy is known and referred to in US20180140755.

Optional features set out below may apply to any aspect of the invention.

The piercing tool may be provided in a sterile package. The sealed package in which the kit is arranged may be sterile.

The piercing tool may have a curved cutting edge. This may be advantageous in terms of cutting a circular aperture, well suited for attachment to a source of negative pressure.

The piercing tool may have a circular cutting edge. This allows a circular aperture to be cut into the wound dressing, to match the shape of a port or airway to be attached over the dressing when connecting it to a source of non-atmospheric pressure.

The piercing tool may comprise a cutting edge and a housing. The cutting edge may be retractable into the housing.

Accordingly, one preferred embodiment of the invention provides a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least one of: a) packaging indicating that the piercing tool is configured to pierce a covering layer of a wound dressing to produce an aperture therein and thereby configure the wound dressing for use in a pressure gradient wound therapy; (b) instructions instructing a user as to how to use the piecing tool to configure a wound dressing for use in a pressure gradient wound therapy system; (c) one or more selectively configurable wound dressings, the wound dressings being configurable for use in a pressure gradient wound therapy system and without a pressure gradient wound therapy system; (d) a source of non-atmospheric pressure; (e) a port for connection to the covering layer of the wound dressing to connect the wound dressing to a source of non-atmospheric pressure; or (f) tubing for connection between a wound dressing and a source of non-atmospheric pressure; the kit being arranged within a sealed package, and the piercing tool comprising a cutting edge and a housing, wherein the cutting edge is retractable into the housing.

The cutting edge may be biased towards a retracted position. The bias may be a spring-bias. The cutting edge may be spring-loaded.

The piercing tool may comprise an actuator. Actuation of the actuator may move the cutting edge to an extended position. The actuator may comprise a button.

The cutting edge may be arranged to extend a predetermined extended distance from the housing in the extended position. This can ensure that the cutting edge is able to cut right through a covering layer of a wound dressing, in order that fluid can pass through the aperture cut into the covering layer, whilst not cutting too deeply into the body of the dressing, so as to reduce damage to internal parts of the dressing, such as a pressure distribution layer, or an absorbent layer. For example, where the piercing tool is for use in a dressing with a pressure distribution layer sandwiched between a covering layer and an absorbent layer, the cutting edge can be arranged to extend through the covering layer, to extend into the pressure distribution layer and not to extend into the absorbent layer.

The predetermined extended distance may be greater than 0.2 mm; greater than 0.5 mm; greater than 1 mm; greater than 1.5 mm; greater than 2 mm; greater than 2.5 mm; greater than 3 mm or greater than 3.5 mm. The predetermined distance may be less than 10 mm; less than 7 mm; less than 5 mm; less than 4 mm; less than 3.5 mm; less than 3 mm; less than 2.5 mm; or less than 1 mm. For example, the predetermined distance may be between 0.5 mm and 2.5 mm, such as between 1 mm and 2 mm, for example about 1.5 mm.

The cutting edge may be arranged to retract a predetermined retracted distance into the housing in the retracted position. This can ensure that in the retracted position (to which the cutting edge is preferably biased) it is sufficiently far into the housing as to reduce the likelihood of any accidental injuries. The predetermined retracted distance may be greater than 1 mm; greater than 1.5 mm; greater than 2 mm; greater than 2.5 mm; greater than 3 mm greater than 3.5 mm; greater than 4 mm or greater than 5 mm. The predetermined distance may be less than 15 mm; less than 12 mm; 10 mm; less than 7 mm; less than 5 mm; less than 4 mm; less than 3.5 mm; less than 3 mm; or less than 2.5 mm. For example, the predetermined distance may be between 5 mm and 10 mm, between 6 mm and 9 mm, for example about 7 mm.

Balancing the distance by which the cutting edge extends against the distance by which it retracts, can produce a compact bespoke piercing tool that is perfectly suited to its purpose.

The housing may be tubular, e.g. cylindrical.

As such, another preferred embodiment of the invention provides a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least one of: a) packaging indicating that the piercing tool is configured to pierce a covering layer of a wound dressing to produce an aperture therein and thereby configure the wound dressing for use in a pressure gradient wound therapy; (b) instructions instructing a user as to how to use the piecing tool to configure a wound dressing for use in a pressure gradient wound therapy system; (c) one or more selectively configurable wound dressings, the wound dressings being configurable for use in a pressure gradient wound therapy system and without a pressure gradient wound therapy system; (d) a source of non-atmospheric pressure; (e) a port for connection to the covering layer of the wound dressing to connect the wound dressing to a source of non-atmospheric pressure; or (f) tubing for connection between a wound dressing and a source of non-atmospheric pressure; the kit being arranged within a sealed package, and the piercing tool comprising a cutting edge and a tubular housing, wherein the cutting edge is retractable into the housing.

The cutting edge may be extendable from one end of the tubular housing. The actuator may be arranged at the opposite end of the tubular housing. A biassing spring may be arranged within the tubular housing between the cutting edge and the actuator.

The housing may comprise a flange. The flange may be an inwardly extending flange. The flange may be annular. The flange may act as a guide.

The flange may support the biasing spring. The biasing spring may be affixed to the flange. The actuator may support the biasing spring. The biasing spring may be affixed to the actuator. The biasing spring may be affixed to the button. For example, one end of the biasing spring may be affixed to the underside of the button and the other end of the biasing spring may be affixed to a topside of the flange.

The actuator may comprise a support extending from the button. The button may have a larger periphery than the support. The support may be tubular, for example cylindrical. The button may be circular. The circular button and cylindrical support may be concentric. The circular button may close one end of the tubular support. The opposite end of the support may be open. The cutting edge may be provided at the base of the support, opposite the button. The cutting edge may be provided on a blade. The cutting edge may be integral with the support. The support may form the blade. The support may support a blade comprising the cutting edge.

The support may be guided by the flange. The outer peripheral surface of the support may be guided by the inner edge of the flange. The button may be guided by the tubular housing. The outer peripheral surface of the button may be guided by the inner tubular surface of the housing.

The cutting edge may have a diameter of at least 5 mm; at least 7 mm; at least 10 mm; at least 15 mm or at least 20 mm. The cutting edge may have a diameter of no more than 50 mm; no more than 30 mm; no more than 25 mm; or no more than 20 mm. For example, the cutting edge may have a diameter of between 5 mm and 50 mm; between 10 mm and 30 mm or between 15 mm and 25 mm, for example about 20 mm.

The button, and/or the housing may have a diameter of at least at least 7 mm; at least 10 mm; at least 15 mm; at least 20 mm or at least 25 mm. The button and/or the housing may have a diameter of no more than 60 mm; no more than 40 mm; no more than 30 mm; or no more than 25 mm. For example, the button and/or the housing may have a diameter of between 7 mm and 60 mm; between 15 mm and 40 mm or between 20 mm and 30 mm, for example about 25 mm.

As noted above, the optional features set out above are equally applicable to all aspects (or embodiments) of the invention (including those set out below).

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least a) packaging indicating that the piercing tool is configured to pierce a covering layer of a wound dressing to produce an aperture therein and thereby configure the wound dressing for use in a pressure gradient wound therapy; the kit being arranged within a sealed package.

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least (b) instructions instructing a user as to how to use the piecing tool to configure a wound dressing for use in a pressure gradient wound therapy system; the kit being arranged within a sealed package.

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least (c) one or more selectively configurable wound dressings, the wound dressings being configurable for use in a pressure gradient wound therapy system and without a pressure gradient wound therapy system; the kit being arranged within a sealed package.

The dressing preferably comprises a pressure distribution layer sandwiched between a covering layer and an absorbent layer, and the cutting edge is preferably arranged to extend through the covering layer, to extend into the pressure distribution layer and not to extend into the absorbent layer.

As such, a preferred embodiment of the invention provides a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and (c) one or more selectively configurable wound dressings, the wound dressings being configurable for use in a pressure gradient wound therapy system and without a pressure gradient wound therapy system and comprising a pressure distribution layer sandwiched between a covering layer and an absorbent layer, and the cutting edge is preferably arranged to extend through the covering layer, to extend into the pressure distribution layer and not to extend into the absorbent layer; the kit being arranged within a sealed package (and optionally including any of features (a), (b), (d), (e) and/or (f) as defined above).

Another preferred embodiment provides a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and (c) one or more selectively configurable wound dressings, the wound dressings being configurable for use in a pressure gradient wound therapy system and without a pressure gradient wound therapy system; wherein the dressing comprises a wound contact layer and a covering layer, the covering layer having a first surface facing the wound contact layer and defining a wound dressing cavity, and a second surface; wherein the second surface of the covering layer comprises an indica, the indica denoting a suitable position in the covering layer to create an aperture to provide fluid communication between the wound dressing cavity and a source of non-atmospheric pressure; wherein the shape and/or size of the indicia matches the shape and/or size of the piercing tool; the kit being arranged within a sealed package (and optionally including any of features (a), (b), (d), (e) and/or (f) as defined above).

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least (d) a source of non-atmospheric pressure; the kit being arranged within a sealed package.

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least (e) a port for connection to the covering layer of the wound dressing to connect the wound dressing to a source of non-atmospheric pressure; the kit being arranged within a sealed package. Preferably the piercing tool is independent of the port. That is to say, preferably the piercing tool is not part of the port, but a separate device not connected to any part of the port. With this arrangement, the port need not be adapted to perform an additional cutting function, and users are less likely to accidentally hurt themselves handling the port (which of course they will not expect to be sharp).

According to an one embodiment of the invention there is provided a packaged kit of parts for use with a selectively configurable wound dressing, the wound dressing being configurable for use in a pressure gradient wound therapy system and without a pressure gradient wound therapy system; the kit comprising: a piercing tool configured to pierce a covering layer of the wound dressing to produce an aperture therein and thereby configure the wound dressing for use in a pressure gradient wound therapy system; and at least (f) tubing for connection between a wound dressing and a source of non-atmospheric pressure; the kit being arranged within a sealed package.

Of course the kit may comprise various combinations of features a to f; for example the kit may comprise at least two features including a+b; the kit may comprise at least two features including a+c; the kit may comprise at least two features including a+d; the kit may comprise at least two features including a+e; the kit may comprise at least two features including a+f; the kit may comprise at least two features including b+c; the kit may comprise at least two features including b+d; the kit may comprise at least two features including b+e; the kit may comprise at least two features including b+f; the kit may comprise at least two features including c+d; the kit may comprise at least two features including c+e; the kit may comprise at least two features including c+f; the kit may comprise at least two features including d+e; the kit may comprise at least two features including d+f; or the kit may comprise at least two features including or e+f. The kit may comprise at least three features including a+b+c; the kit may comprise at least three features including a+b+d; the kit may comprise at least three features including a+b+e; the kit may comprise at least three features including a+b+f; the kit may comprise at least three features including a+c+d; the kit may comprise at least three features including a+c+e; the kit may comprise at least three features including a+c+f; the kit may comprise at least three features including a+d+e; the kit may comprise at least three features including a+d+f; the kit may comprise at least three features including a+e+f; the kit may comprise at least three features including b+c+d; the kit may comprise at least three features including b+c+e; the kit may comprise at least three features including b+c+f; the kit may comprise at least three features including b+d+e; the kit may comprise at least three features including b+d+f; the kit may comprise at least three features including b+e+f; the kit may comprise at least three features including c+d+e; the kit may comprise at least three features including c+d+f; the kit may comprise at least three features including c+e+f; or the kit may comprise at least three features including d+e+f. The kit may comprise at least four features including a+b+c+d; the kit may comprise at least four features including a+b+c+e; the kit may comprise at least four features including a+b+c+f; the kit may comprise at least four features including b+c+d+e; the kit may comprise at least four features including b+c+d+f: the kit may comprise at least four features including b+d+e+f: or the kit may comprise at least four features including c+d+e+f. The kit may comprise at least five features including a+b+c+d+e; the kit may comprise at least five features including a+b+c+d+f; the kit may comprise at least five features including a+b+c+e+f; the kit may comprise at least five features including a+b+d+e+f; the kit may comprise at least five features including a+c+d+e+f; or the kit may comprise at least five features including b+c+d+e+f. The kit may comprise all six features; a+b+c+d+e+f.

One particular embodiment includes at least one item selected from a+b; one particular embodiment includes at least one item selected from a+c; one particular embodiment includes at least one item selected from a+d; one particular embodiment includes at least one item selected from a+e; one particular embodiment includes at least one item selected from a+f; one particular embodiment includes at least one item selected from b+c; one particular embodiment includes at least one item selected from b+d; one particular embodiment includes at least one item selected from b+e; one particular embodiment includes at least one item selected from b+f; one particular embodiment includes at least one item selected from c+d; one particular embodiment includes at least one item selected from c+e; one particular embodiment includes at least one item selected from c+f; one particular embodiment includes at least one item selected from d+e; one particular embodiment includes at least one item selected from d+f; one particular embodiment includes at least one item selected from e+f; one particular embodiment includes at least one item selected from a+b+c; one particular embodiment includes at least one item selected from a+b+d; one particular embodiment includes at least one item selected from a+b+e; one particular embodiment includes at least one item selected from a+b+f; one particular embodiment includes at least one item selected from a+c+d; one particular embodiment includes at least one item selected from a+c+e; one particular embodiment includes at least one item selected from a+c+f; one particular embodiment includes at least one item selected from a+d+e; one particular embodiment includes at least one item selected from a+d+f; one particular embodiment includes at least one item selected from a+e+f; one particular embodiment includes at least one item selected from b+c+d; one particular embodiment includes at least one item selected from b+c+e; one particular embodiment includes at least one item selected from b+c+f; one particular embodiment includes at least one item selected from b+d+e; one particular embodiment includes at least one item selected from b+d+f: one particular embodiment includes at least one item selected from b+e+f; one particular embodiment includes at least one item selected from c+d+e; one particular embodiment includes at least one item selected from c+d+f; one particular embodiment includes at least one item selected from c+e+f; one particular embodiment includes at least one item selected from d+e+f; one particular embodiment includes at least one item selected from a+b+c+d; one particular embodiment includes at least one item selected from a+b+c+e one particular embodiment includes at least one item selected from a+b+c+f; one particular embodiment includes at least one item selected from b+c+d+e; one particular embodiment includes at least one item selected from b+c+d+f; one particular embodiment includes at least one item selected from b+d+e+f; one particular embodiment includes at least one item selected from c+d+e+f; one particular embodiment includes at least one item selected from a+b+c+d+e; one particular embodiment includes at least one item selected from a+b+c+d+f; one particular embodiment includes at least one item selected from a+b+c+e+f; one particular embodiment includes at least one item selected from a+b+d+e+f; one particular embodiment includes at least one item selected from a+c+d+e+f; one particular embodiment includes at least one item selected from b+c+d+e+f.

The packaging may for example be cardboard packaging. The packaging may comprise printed information indicating that the wound dressing is selectively configurable for use in a pressure gradient wound therapy system and without a pressure gradient wound therapy system. The packaging may be sterile; and/or at least part of the packaging, or a sub-package may be sterile.

The instructions instructing a user as to how to configure the wound dressing for use in a pressure gradient wound therapy system and for use without a pressure gradient wound therapy system may be printed on packaging. The instructions instructing a user as to how to configure the wound dressing for use in a pressure gradient wound therapy system and for use without a pressure gradient wound therapy system may be provided on an instruction sheet (which where the kit includes features a+b may be provided in the packaging).

The source of non-atmospheric pressure preferably a source of negative pressure. Alternatively it may be a source of positive pressure. The source of non-atmospheric pressure may be a pump.

The port for connection to the covering layer of the wound dressing to connect the wound dressing to a source of non-atmospheric pressure may be provided with an airway. Thea airway may be a transparent passageway securable to the outside of the cover layer at the proximal end of the conduit so as to surround the aperture in the cover layer from above. The port/airway may comprise a connector, at its distal end, for connecting the dressing to a source of pressure (either positive or negative), for example a pump. Preferably the connector is a luer lock to facilitate secure connection to the pump and to maintain the pressure within the wound dressing while the pump is temporarily disconnected. The connector preferably comprises a one-way lock to assist in the maintenance of the applied pressure. To resist collapse, the airway may comprise an internal cylinder of nylon fibres to maintain openness of the airway to fluid.

The tubing for connection between a wound dressing and a source of non-atmospheric pressure may be transparent tubing. The tubing may be flexible. The tubing may be resilient. The tubing may be formed from a resilient flexible plastics material.

As for the wound dressing:

The wound dressing may comprise a covering layer. The wound dressing may comprise a pressure distribution layer. The covering layer may define a cavity. The pressure distribution layer may be provided in, e.g. contained in, the cavity. The wound dressing may comprise an indica. The indicia may be a mark. The mark may be formed of ink or dye, for example the indicia may be printed. The mark may be formed by discoloration, e.g. the indicia could be laser marked. The indicia may be visible on an outside surface of the covering layer. The covering layer may comprise the indicia. The indica may denote a position (for example a suitable position or the optimal position) in the covering layer to create an aperture to provide fluid communication between the pressure distribution layer and a source of non-atmospheric pressure.

The shape of the indicia may match the shape of the piercing tool. The shape of the indicia may match the shape of the cutting edge. The shape of the indicia may match the shape of the housing. The size of the indicia may match the size of the piercing tool. The size of the indicia may match the size of the cutting edge. The size of the indicia may match the size of the housing. By matching the shape and/or size of the indicia to the shape and/or size of the piercing tool, it is straightforward for the user to align the piercing tool with the position denoted by the indicia where the wound dressing should be pierced to cut an aperture therein and thereby configure it for use in a pressure gradient wound therapy system.

In one embodiment the wound dressing may comprise a wound contact layer and a covering layer, the covering layer having a first surface facing the wound contact layer and defining a wound dressing cavity, and a second surface; wherein the second surface of the covering layer comprises an indica, the indica denoting a suitable, or more preferably an optimal, position in the covering layer to create an aperture to provide fluid communication between the wound dressing cavity and a source of non-atmospheric pressure.

In one embodiment the wound dressing may comprise a pressure distribution layer and a covering layer; wherein the covering layer comprises an indica, the indica denoting the optimal position in the covering layer to create an aperture to provide fluid communication between the pressure distribution layer and a source of non-atmospheric pressure.

The indicia may be printed onto for example the covering layer. Alternatively the indicia/mark could be applied by other means, as outlined above. The covering layer may have an upper side and an underside. The indicia may be applied onto the upper side of the covering layer. The indicia may be applied onto the underside of the covering layer. The covering layer may be transparent or translucent (this would allow indicia to be visible even if printed onto the underside).

The indicia is preferably located out of alignment (i.e. vertical alignment in use) with the centre of the dressing. For example it may be located towards the periphery of the covering layer and/or the pressure distribution layer (or the wound when in use). This assists in the spread of exudate across the full extent of the pressure distribution layer (and across an absorbent layer where an absorbent layer is provided).

The pressure distribution layer may be provided adjacent to the cover layer. The covering layer may define a cavity. The pressure distribution layer may be provided in, e.g. contained in, the cavity. The pressure distribution layer may be gas and liquid permeable and particularly moisture vapour permeable. The pressure distribution layer serves to aid access of exudate to a greater area of the absorbent layer by allowing it to spread under the distribution layer. The pressure distribution layer also serves to even out the negative pressure applied to the wound over the whole dressing (when used for NWPT). The pressure distribution layer is preferably configured to distribute exudate and negative pressure over the dressing. The pressure distribution layer preferably has an open structure when under negative pressure. The layer preferably wicks fluid but has low fluid absorption properties so that the open spaces do not become blocked with exudate as this can prevent air and fluid flow through the dressing. The pressure distribution layer is preferably a foam layer such as a polyester foam of the type XD4200AS manufactured by Caligen or another suitable reticulated foam, such as a hydrophilic non-swelling reticulated foam, e.g. the SAQ series manufactured by INOAC, or hydrophobic reticulated polyester polyurethane foam, e.g. that sold under the designation S90M from INOAC. Alternatively, the pressure distribution layer could be a 3D spacer fabric, or a knitted or mesh fabric.

An adhesive layer may be provided so as to form an adhesive border. The adhesive layer may be provided on the underside of the covering layer. The adhesive border may be provided at the periphery of the dressing arranged to adhere the dressing to the skin surrounding the wound to form a fluid tight seal. The adhesive layer may be provided with perforations to assist transport of exudate and fluid through the dressing. The adhesive layer may also be applied to any of the other layers to provide an island configuration.

The indicia may be located in a region of the covering layer within that defined by the adhesive border. For example it may be located towards the periphery of the region of the covering layer inwards of the adhesive border.

In the configuration for use without a pressure gradient wound therapy system the region of the covering layer within that defined by the adhesive border may be closed, sealed and/or uninterrupted, e.g. a continuous unbroken membrane. This restricts/prevents microbes, bacteria or the like from entering the wound dressing and hence from entering the wound. In the configuration for use with a pressure gradient wound therapy system the region of the covering layer within the adhesive border may be interrupted by an opening, the opening being an aperture in the region of the indicia for connection to a source of non-atmospheric pressure. This allows non-atmospheric pressure to be applied to the wound.

The wound dressing may include a dressing body comprising an absorbent material for contacting the wound, i.e. which may be positioned in contact with a wound, in use. The dressing body may be formed from one of more layers. The dressing body may be configured to absorb exudate from the wound, aided by the action of a connected pump assembly. The dressing body may comprise an absorbent foam material, for example a layer of absorbent foam material. The foam material may comprise a superabsorbent material, for example a superabsorbent foam material. The dressing body may be formed of a hydrocolloid material which may gel in the presence of an exudate. The hydrocolloid material may comprise a layer or multiple layers of gelling fibres and absorbent materials. The covering layer may be constructed of a thin film layer (e.g. a polyurethane) enabling moisture vapour to exit the dressing at an increased rate. This combination is particularly suitable for allowing the wound therapy apparatus to manage fluid without the need of a canister. This may be referred to as a "canister-less" or "canister-free" system. In a variant, the wound dressing may be operable to be fluidly connected to a canister into which exudate removed from the wound may be withdrawn. The adhesive border may define an interior region of the wound dressing. The dressing body may be provided in the interior region of the wound dressing.

The wound dressing may comprise a release layer, the release layer being removable to reveal the adhesive border.

The wound dressing may have a thickness between 1 mm to 20 mm, or 2 mm to 10 mm, or 3 mm to 7 mm, for example.

The pressure distribution layer may be a foam layer. The wound dressing may comprise the outer cover layer, the pressure distribution layer, one or more absorbent layer(s) and a silicone gel wound contact layer. The wound dressing may comprise an outer cover layer and one or more absorbent layer(s) in combination with a gel-forming fibre. The gel-forming fibre typically is in direct contact with the wound, and thus no additional wound contact layer is required i.e., a silicone gel wound contact layer does not require a silicone gel layer.

Gel-forming fibres include hygroscopic fibres which upon the uptake of wound exudate become moist slippery or gelatinous. The gel forming fibres can be of the type which retain their structural integrity on absorption of exudate or can be of the type which lose their fibrous form and become an amorphous or structureless gel. The gel forming fibres are preferably sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

The gel forming fibres are preferably chemically modified cellulosic fibres in the form of a fabric and in particular carboxymethylated cellulose fibres as described in PCT WO00/01425 to Azko Nobel UK Ltd, and can be provided by a layer of gel forming fibres preferably located in a port of the cover layer or as a layer of fibres in a conduit of the wound dressing. When present in the conduit, the layer of fibres can also serve to keep the conduit open to the passage of fluid in the event that the conduit is kinked or otherwise restricted by being lain on or leaned on by the user. The carboxymethylated cellulosic fabrics preferably have a degree of substitution between 0.12 to 0.35 as measured by IR spectroscopy (as defined in WO00/01425) more preferably a degree of substitution of between 0.20 and 0.30 and are made by carboxymethylating a woven or non-woven cellulosic fabric such that the absorbency is increased. Particular preferred fabrics have an absorbency of between 10 g/g of sodium/calcium chloride as defined above to 30 g/g of sodium/calcium chloride as measured by the method described in BS EN 13726-1 (2002) "Test methods for primary wound dressings", section 3.2 "Free swell absorptive capacity". Particularly preferred fabrics have an absorbency of 15 g/g to 25 g/g and most preferred of 15 g/g to 20 g/g of sodium/calcium chloride as measured by the method defined above.

The cellulosic fabric preferably consists solely of cellulosic fibre but may contain a proportion of non-cellulosic textile fibre or gel forming fibre. The cellulosic fibre is of known kind and may comprise continuous filament yarn and/or staple fibre. The carboxymethylation is generally performed by contacting the fabric with an alkali and a carboxymethylating agent such a chloracetic acid in an aqueous system. The fabric is preferably of a non-woven type to reduce shedding in the wound on cutting the dressing. Preferably the fabric is hydroentangled and thus comprises a series of apertures on a microscopic scale.

Where present, the absorbent layer of the wound dressing is capable of absorbing exudate from the wound and allowing the passage of fluid through it. The absorbent layer can comprise any absorbent capable of absorbing exudate while allowing the passage of fluid through it, such as a foam, sponge or fibre-based material, preferably the absorbent layer is provided by gel forming fibres of the same type or of a different type as those discussed above. The gel-forming fibres are hygroscopic fibres which upon the uptake of wound exudate become moist slippery or gelatinous and thus reduce the tendency for the surrounding fibres to adhere to the wound. The gel forming fibres are preferably spun sodium carboxymethylcellulose fibres, chemically modified cellulosic fibres, alkyl sulphonate modified cellulosic fibres such as those described in WO2012/061225, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit and more preferably are lightly substituted so that the absorbency of the fibres is limited. The gel forming fibres preferably have an absorbency of at least 2 grams 0.9% saline solution per gram of fibre (as measured by the method described above) but less than 30 grams 0.9% saline solution per gram of fibre. The gel forming fibres are preferably carboxymethylated cellulose fibres as described in PCT WO00/01425 to Azko Nobel UK Ltd which describes lightly carboxymethylated cellulose fabrics. The gel forming fibres are preferably lightly carboxymethylated in order to reduce the tendency of the absorbent layer to gel block and block the pathway for fluid from the wound, e.g. through the absorbent layer, the port and to a distal end of the conduit.

Preferably an absorbent layer is provided with fenestrations to aid the application of negative pressure to the wound and maintain the pathway for fluid from the wound, through the absorbent layer. Typically, however, fenestrations are only provided in internal absorbent layers.

Although the absorbent layer can be in direct contact with the wound, preferably the dressing comprises a wound contact layer, positioned between the wound and the absorbent layer(s). The wound contact layer may be capable of absorbing exudate from the wound and transmitting it to the absorbent layer. Thus, there may be provided "internal" absorbent layers as defined above, preferably including fenestrations and an external absorbent layer, which forms the wound contact layer. Like the internal absorbent layer, the wound contact layer may be capable of allowing the passage of fluid through it so that pressure (either positive or negative) may applied to the wound and the pathway for fluid/exudate from the wound to the distal end of the conduit may be maintained.

The wound contact layer may include gel-forming fibres (e.g. of the type discussed herein), or a silicone gel, for example.

Preferably the wound contact layer comprises gel-forming fibres. The gel-forming fibres may be the same or a similar type to those comprising the absorbent layer but the wound contact layer may be strengthened to increase its integrity and that of the dressing. For example, the wound contact layer may be of the type described in EP 1904011 and comprise gel-forming fibres in the form of a mat with lines of longitudinal stitching made of cellulose or nylon or polyolefin yarn to increase the integrity of the layer. Preferably the wound contact layer is porous to maintain the pathway for fluid/exudate from the wound to the distal end of the conduit.

Preferably the one or more absorbent layer(s) comprise an internal absorbent layer provided with fenestrations to aid the application of negative pressure to the wound and maintain the pathway for fluid from the wound, through the internal absorbent layer and a wound contact layer comprising gel-forming fibres is also provided.

The (outer) covering layer of the dressing is provided as a bacterial and viral barrier layer which preferably resists the ingress of liquid and air but allows moisture vapour transmission. In this way the covering layer enhances the overall fluid handling capacity of the dressing by allowing for the escape of moisture vapour through the cover while enabling the application of pressure (either positive or negative) to the wound. The outer covering layer is for instance a layer having a MVTR of at least 10,000 g $m^{-2}$ per 24 hours or in the range of from 10,000 $gm^{-2}$ to 50,000 g $m^{-2}$ per 24 hours measured by the method described in BS EN 13726-2 2002 "Test methods for primary wound dressings Part 2 Moisture vapour transmission rate of permeable film dressings". The covering layer may be in the form of a film of polyurethane, for example Epurex 912 T/129 manufactured by Covestro or Inspire 2350 manufactured by Coveris or Medifilm 426 manufactured by Mylan. Alternatively the covering layer may be in the form of a film of polyethylene.

The wound dressing preferably is a one-piece dressing. That is to say, it is the covering layer and the body of the wound dressing are provided as an integral item, preferably including an adhesive layer and preferably including a removable release layer. The body of the wound dressing that is provided, along with the covering layer, as an integral item may comprise the pressure distribution layer.

The one-piece dressing may be provided in a package. The package may be a sterile package.

According to another aspect of the invention there is provided a pressure gradient wound therapy apparatus, comprising the kit of any preceding aspect of the invention.

In embodiments, the wound therapy apparatus comprises a negative pressure wound therapy apparatus. In other embodiments, the wound therapy apparatus comprises a positive pressure wound therapy apparatus.

In embodiments, the apparatus may comprise a canister and the wound dressing may be fluidly connected to the canister into which exudate removed from the wound may be withdrawn. In preferred embodiments, the wound dressing may be formed of a hydrocolloid material which may gel in the presence of an exudate and the apparatus may include no cannister. This may be referred to as a "canister-less" system.

The pump assembly may be fluidly connected to an interior region of the wound dressing, for introducing and/or removing gas from within the wound dressing to control the pressure therein.

According to a further broad aspect of the invention there is provided a method of configuring a selectively configurable wound dressing, the wound dressing being configurable for use in a pressure gradient wound therapy system and without a pressure gradient wound therapy system; the method comprising configuring the wound dressing for use with a pressure gradient wound therapy system by cutting an aperture in the wound dressing.

According to an aspect of the invention there is provided a method of configuring a selectively configurable wound dressing, the wound dressing comprising a covering layer and being configurable for use in a pressure gradient wound therapy system and without a pressure gradient wound therapy system; the method comprising configuring the wound dressing for use with a pressure gradient wound therapy system by cutting an aperture in the covering layer of the wound dressing using a piercing tool.

Of course, the piercing tool of the method aspects may be the piercing tool of the aspects of invention set out above.

And again, of course the wound dressing may comprise any optional feature described above.

For example, the wound dressing may comprise a covering layer, which comprises an indica denoting an optimal position in the covering layer to create an aperture to provide fluid communication between the dressing (e.g. a pressure distribution layer thereof) and a source of non-atmospheric pressure; the method comprising configuring the wound dressing for use with a pressure gradient wound therapy system by cutting an aperture in the covering layer of the wound dressing in the region of the indicia.

Likewise, the wound dressing may comprise a pressure distribution layer, in which case the method may comprise not cutting into the pressure distribution layer, or cutting into but not cutting through the pressure distribution layer. Similarly, the wound dressing may comprise a wound contact layer and the method may comprise not cutting into the wound contact layer, or cutting into, but not cutting through the wound contact layer. The wound dressing may comprise a pressure distribution layer and a wound contact layer and the method may comprise cutting through the covering layer, cutting into, but not through, the pressure distribution layer, and not cutting into the wound contact layer.

The wound dressing may comprise a release layer and the method may comprise cutting the aperture, then removing the release layer, then applying the dressing to a wound.

The method may be a method of re-purposing a wound dressing that is provided on a wound and configured for use without a pressure gradient wound therapy system; the method comprising cutting an aperture in the wound dressing (in-situ) using the piercing tool in order to configure the wound dressing for use with a pressure gradient wound therapy system.

The method may comprise attaching a non-atmospheric pressure source to the wound dressing after configuring the wound dressing for use with a pressure gradient wound therapy system.

DETAILED DESCRIPTION OF THE INVENTION

In order that the invention may be more clearly understood one or more embodiments thereof will now be described, by way of example only, with reference to the accompanying drawings, of which:

Figure 6:
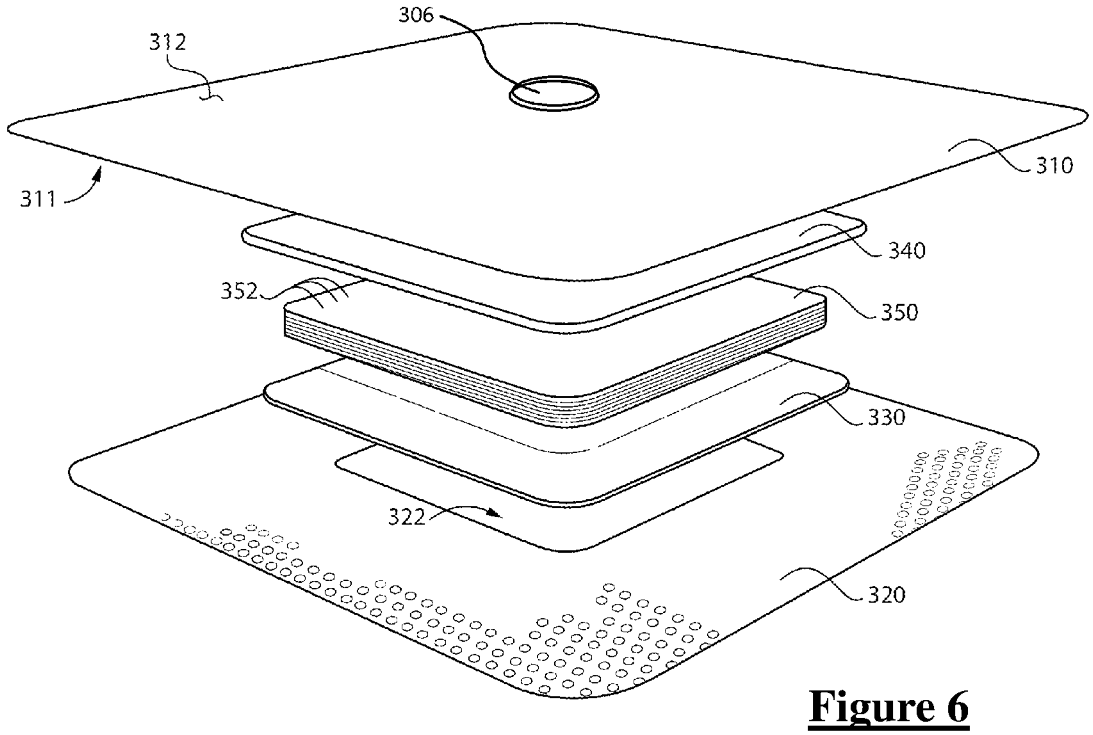
FIG. 6 is an exploded view of the embodiment of the wound dressing of FIG. 3 configured for use with a pressure gradient wound therapy apparatus
Figure 4:
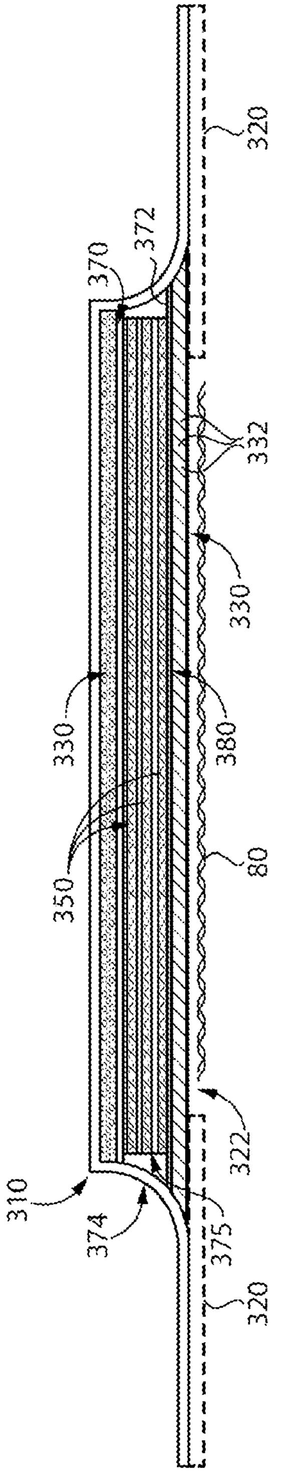
FIG. 4 is a cross-sectional view of the wound dressing illustrated in FIG. 3.
Figure 7A:
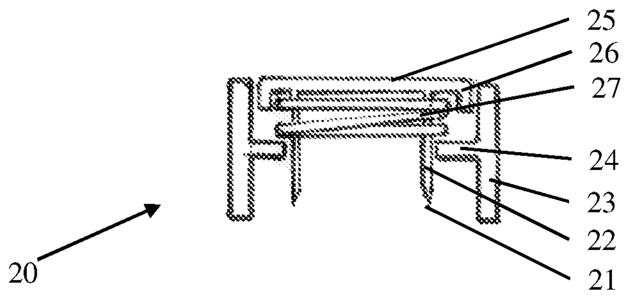
FIG. 7*a* is a cross section through a piercing tool.
Figure 7B:
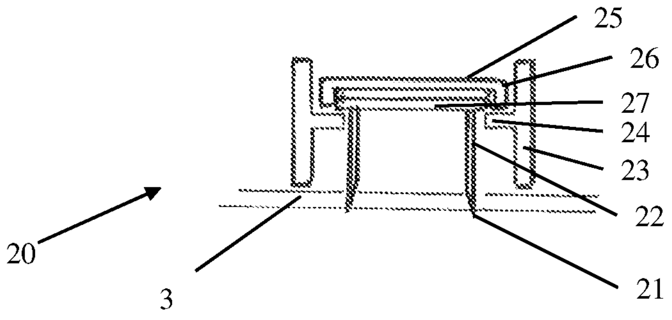
Figure 8:
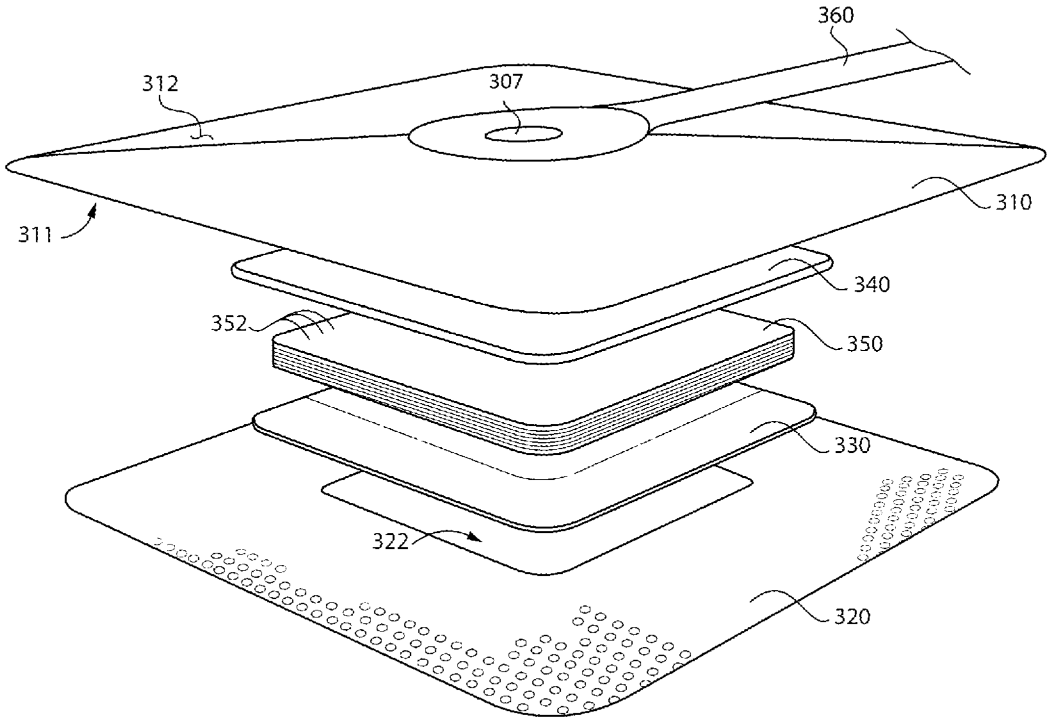
Figure 9:
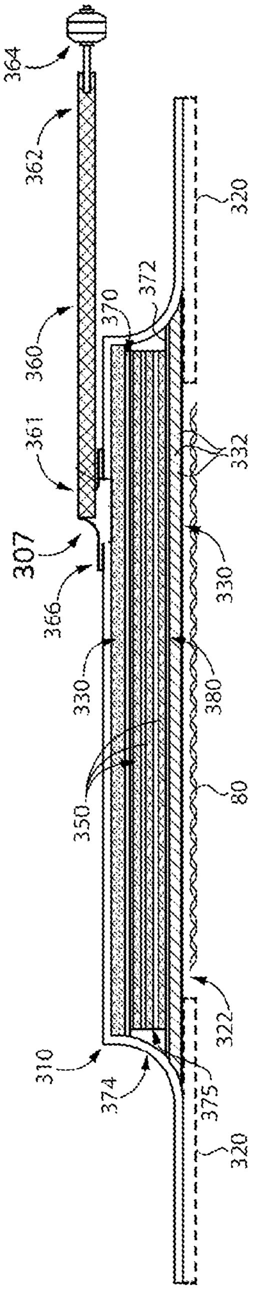
Figure 10:
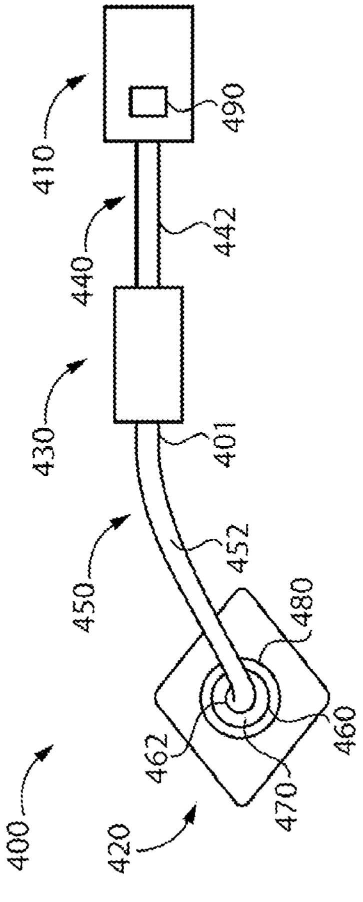
Figure 11:
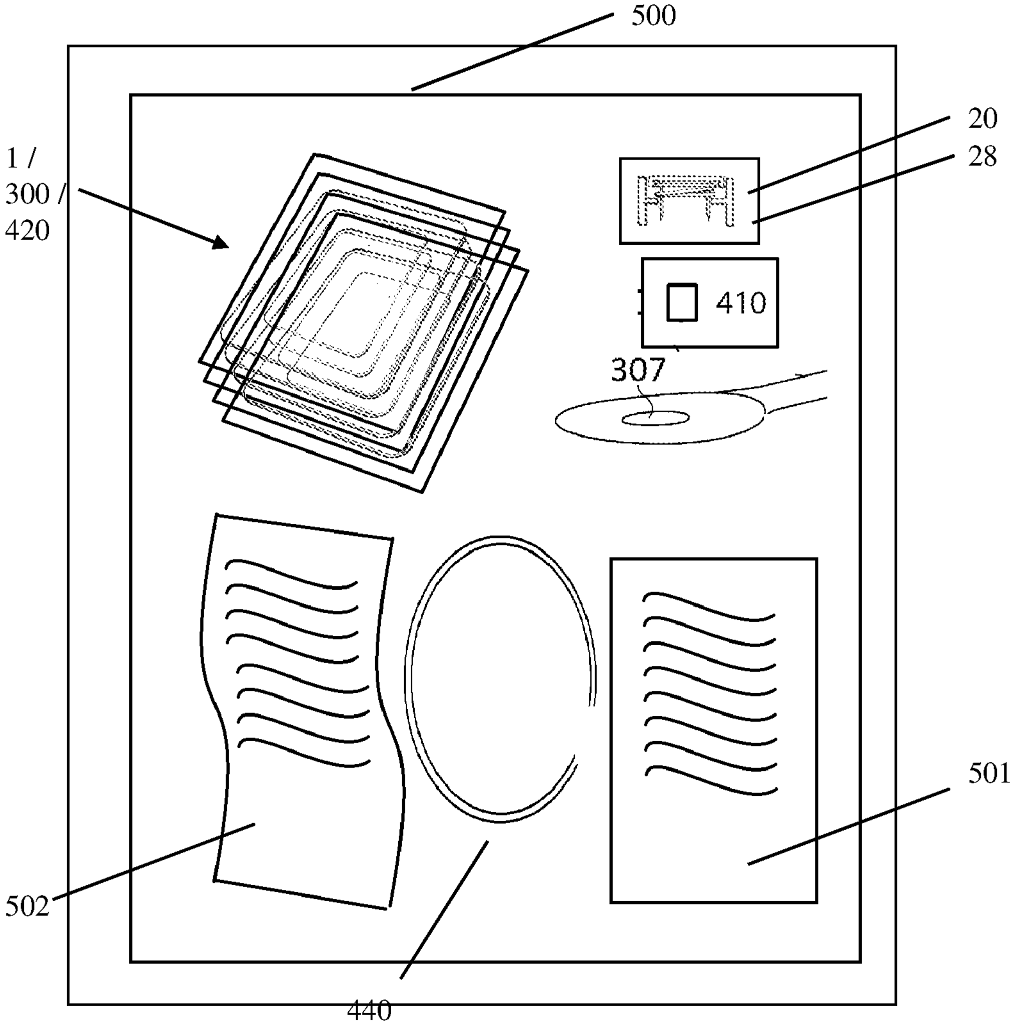

FIG. 7*b* is a cross section through the piercing tool of FIG. 7*a* in a piercing configuration;

FIG. 8 is an exploded view of the wound dressing of FIG. 6 in use with a pressure gradient wound therapy apparatus;

FIG. 9 is a cross-sectional view of the wound dressing of FIG. 4 in use with a pressure gradient wound therapy apparatus;

FIG. 10 is a schematic representation of a wound exudate management system according to certain embodiments; and FIG. 11 is a schematic representation of a kit of parts.

Embodiments disclosed herein relate to apparatus and methods of treating a wound both with and without reduced or positive pressure (typically negative pressure). Some embodiments including pump and wound dressing component. The wound dressings discussed are "one-piece" dressings incorporating both a covering layer and an absorbent body.

As disclosed herein the present invention may comprise a piercing tool; or a kit comprising the piercing tool and other apparatus for providing pressure gradient wound therapy to a wound.

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds (either as a result of surgery, trauma, stemiotomies, fasciotomies, or other conditions), dehisced wounds, acute wounds, chronic wounds, subacute and dehisced wounds, traumatic wounds (such as from orthopaedic trauma), flaps and skin grafts, lacerations, abrasions, contusions, burns, diabetic ulcers, pressure ulcers, stoma, surgical wounds, trauma and venous ulcers, broken bones or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

The technology disclosed can be used on an acute or chronic wound.

Wounds are believed to be more susceptible to infection under the following circumstances. If the wounds are chronic wounds, or if an object which caused the wound was dirty or contained bacteria, or from a bite, or contains remnant or a whole object that caused the wound, or a wound that is large or deep, or jagged edges to the wound, or elderly, or chronic because by their nature a wound site is open; and/or if the patient has: diabetes type 1 or type 2, is elderly, or has a compromised immune system.

Pressure gradient wound therapy may also be useful for treating second- and third-degree burns, as well as being useful for laparotomy surgery i.e., a large incision through an abdominal wall to gain access into the abdominal cavity.

Figure 1:
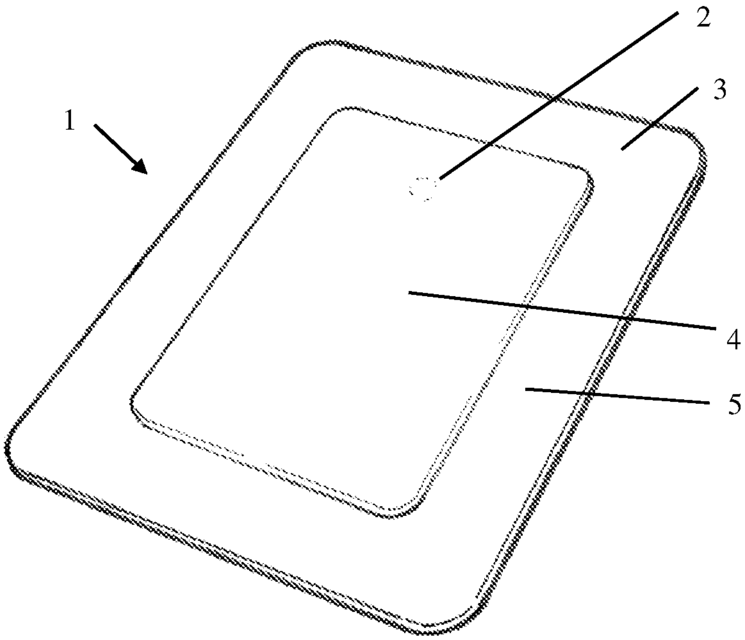
FIG. 1 is a schematic representation of an embodiment of a wound dressing configured for use without a wound therapy apparatus.
Figure 2:
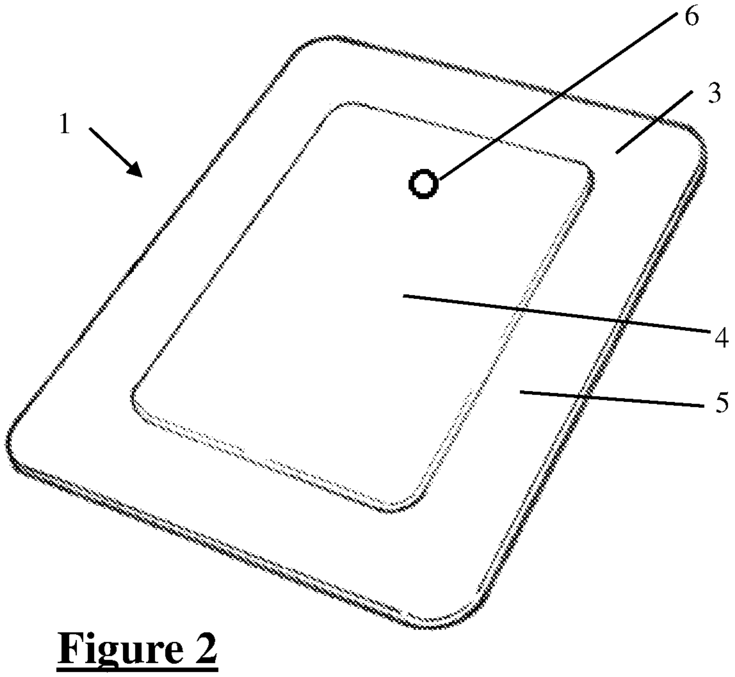
FIG. 2 is a schematic representation of the wound dressing of FIG. 1 configured for use with a wound therapy apparatus.

FIGS. 1 and 2 illustrates an embodiment of a wound dressing 1 for use in accordance with the invention in two different configurations.

In general, the invention relates to the piercing tool 20 (of FIGS. 7*a* and 7*b*) which is used in configuration of a wound dressing 1, the wound dressing 1 being selectively configurable for use without a pressure gradient wound therapy system or for use with a pressure gradient wound therapy system, e.g. negative pressure wound therapy.

As shown in FIG. 1, the wound dressing 1 includes an optional indicia 2 visible on the upper (outside) surface of a covering layer 3 of the dressing 1. The covering layer 3 has a raised central region 4, where it overlies a dressing body, which can include a pressure dispersion layer; an absorbent/superabsorbent layer/layers; and a wound-contact layer. The dressing 1 also has a border region 5, where it overlies an adhesive layer. A removable release layer (not shown) is provided on the underside.

The indicia 2 indicates where the dressing should be cut to form an aperture in order to configure the dressing for use with a pressure gradient wound therapy system; the dressing being configured for use without a pressure gradient wound therapy system unless/until an aperture is cut in the covering layer. In this embodiment, the indicia 2 is shown as a circle formed in dashed lines, arranged in the optimal position for connection of a source of non-atmospheric pressure. Obviously in other embodiments alternative shapes/signs could be used and of course the indicia need not be in dashed lines.

Moreover it is contemplated that the piercing tool 20 may be used with dressings not having an indicia at all, with the user following instructions, in order to pierce the covering layer in a suitable location (e.g. the region shown by reference numeral 2).

As illustrated in FIG. 1, the wound dressing 1 is configured for use without a pressure gradient wound therapy system. To use the wound dressing 1 without a pressure gradient wound therapy system, the release layer is simply removed and the dressing applied in the same way as an ordinary wound dressing. It will be noted that the entire raised central region 4 of the covering layer 3 is a continuous unbroken membrane, uninterrupted and closed, so that the wound (within the region defined by the adhesive border) is in a sealed environment, restricting/preventing bacteria/microbes entering the wound and causing infection.

FIG. 2 shows the wound dressing 1 of FIG. 1 configured for use with a pressure gradient wound therapy system. Here, a user has cut through the cover layer 3 using the piercing tool 20 in the region of the indicia 2, to form an aperture 6 in the wound dressing 1 (so that the central region 4 is no longer closed/uninterrupted). With the wound dressing 1 now configured for use with a pressure gradient therapy system, a source of non-atmospheric, e.g. negative, pressure can be connected to the aperture 6 to aid the wound-healing process.

For example, a port (not shown in FIG. 1 or 2) can be adhered to the wound dressing 1, such that a conduit through the port is aligned with the aperture 6; the port can be connected via tubing (also not shown in FIGS. 1 and 2) to a pump (also not shown in FIGS. 1 and 2) producing negative pressure.

The piercing tool 20 (best seen in FIGS. 7*a* and 7*b*) is specially configured to pierce the covering layer of a wound dressing, whilst not cutting too deeply into the dressing. The piercing tool 20 may be provided in a sterile package and as part of a kit, as discussed in more detail below, with reference to FIG. 11.

The piercing tool 20 of this embodiment is intended to cut a circular aperture, and therefore has a curved cutting edge 21, which defines a circle (to allow a circular aperture to be cut into the wound dressing, to match the shape of a port or airway to be attached over the dressing when connecting it to a source of non-atmospheric pressure).

The cutting edge 21 of this embodiment is provided at the end of a tubular support 22, the tubular support 22 being cylindrical and the edge formed by sharpening one end of the cylindrical tube. The tubular support 22 and cutting edge 21 can be formed from metal and may be considered similar to a circular metal pastry cutter, albeit smaller (typically between 15 mm and 25 mm, for example about 20 mm) and with a much sharper cutting edge, akin to a scalpel for example. In this way, the support 22 itself forms a blade, the blade having a cutting edge. In the alternative, the support 22 could carry a separate blade, the separate blade comprising the cutting edge. This would allow for the support to be integrated with other parts of the piercing tool (e.g. the button discussed below, formed for example from plastic).

The tubular support 22 of the embodiment is arranged within a housing 23. In such a way that the cutting edge can extend from a base of the housing 23 in use, and when not in use, is retracted into the housing 23.

The housing 23 of this embodiment is also tubular, with a wider diameter than the support 22 that it houses, and an inwardly extending flange 24 arranged approximately halfway along the length of the housing. The flange 24 is annular, with an inner diameter slightly larger than the outer diameter of the support 22, so as to act as a guide for the support 22 when the cutting edge 21 is moved between the extended and retracted positions. The outer peripheral surface of the support 22 is guided by the inner edge of the flange 24.

In order for a user to move the cutting edge 21 between the retracted and extended positions, the piercing tool 20 is provided with an actuator, which in this embodiment includes a circular button 25. The circular button 25 is arranged at the opposite end of the support 22 to the cutting edge 21. The circular button 25, may be formed integrally with the metal support 22 or formed separately, for example from plastic and attached to the support, e.g. by adhesive. The button 25, support 22 and tubular housing 23 are conveniently arranged coaxially/concentrically.

The button 25 of this embodiment of the invention has a larger periphery than the support 22, thus it closes one end of the tubular support 22 and extends beyond the outer periphery of the tubular support 22. At the periphery of the button, a downwardly extending lip 26 is provided. The outer peripheral surface of the button 25, i.e. that of the lip 26 is guided by the inner circumferential surface of the tubular housing 23, and in this embodiment, in the retracted position, the upper surface of the button 25 is aligned with the upper end of the tubular housing 23.

The size of the button 25 and the housing 23 are determined by the size of the cutting edge 21, which in turn is determined by the size of the aperture that it is desired to cut. So, for example, the button can have an outer diameter of 1-20 mm larger than the support, and the housing can have a diameter of 1-20 mm larger than the button. Thus, in this exemplary embodiment with a cutting edge of 20 mm, the diameter of the button may be 22 mm and the outer diameter of the housing may be 25 mm.

The cutting edge 21 is biased towards a retracted position, this is achieved by spring-loading the button 25 towards the retracted position using a compression spring 27 arranged within the housing between the actuator and the cutting edge 21. The compression spring 27 is affixed at one end to the topside of the flange and at its opposite end to the underside of the button 25.

A clip, retaining lug, or the like (not shown) between the support 22 and the flange 24, and/or between the button 25 and the housing 23 can be provided to prevent the actuator from falling out of the top of the housing 23 or the spring could be attached, e.g. glued to both the topside of the flange and the underside of the button to join the parts.

The length of the housing 23 relative to the support 22 determines the distance that the cutting edge 21 can be retracted into the housing when in the retracted position. As shown, when in the retracted position, the top surface of the button 25 and the housing 23 may be coplanar. This predetermined retracted position can be determined so as to ensure that the user is unlikely to cut themselves on the blade, and for example might be greater than 1 mm; greater than 1.5 mm; greater than 2 mm; greater than 2.5 mm; greater than 3 mm greater than 3.5 mm; greater than 4 mm or greater than 5 mm. The predetermined distance may be less than 15 mm; less than 12 mm; 10 mm; less than 7 mm; less than 5 mm; less than 4 mm; less than 3.5 mm; less than 3 mm; or less than 2.5 mm. For example, the predetermined distance may be between 5 mm and 10 mm, between 6 mm and 9 mm, for example about 7 mm. Providing the button 25 flush (or below) the top surface of the housing 23, helps prevent the button 25 being accidentally depressed.

The distance to which the cutting edge can extend is determined by the length of the support and the housing, and also the distance between the actuator and the flange 24 (and any space taken up by the compression spring 27).

It is important that this predetermined extended distance by which the cutting edge 21 extends from the base of the housing 23 is carefully controlled, so as to control how far into the wound dressing the cutting edge 21 extends.

As shown in FIG. 7*b*, in the extended position, the cutting edge 21 cuts right through the covering layer 3 of a wound dressing, but not into any layer beneath. Alternatively, for example, where the piercing tool is for use in a dressing with a pressure distribution layer sandwiched between a covering layer and an absorbent layer (as discussed below with reference to FIGS. 3-6), the cutting edge 21 can be arranged to extend through the covering layer 310, to extend into the pressure distribution layer 340 and not to extend into the absorbent layer(s) 350 (or the wound contact layer 330).

This means that fluid can pass through the aperture cut into the covering layer, whilst not cutting too deeply into the body of the dressing, so as to reduce damage to internal parts of the dressing, such as a pressure distribution layer, or an absorbent layer.

As an example, the predetermined extended distance may be greater than 0.2 mm; greater than 0.5 mm; greater than 1 mm; greater than 1.5 mm; greater than 2 mm; greater than 2.5 mm; greater than 3 mm or greater than 3.5 mm. The predetermined distance may be less than 10 mm; less than 7 mm; less than 5 mm; less than 4 mm; less than 3.5 mm; less than 3 mm; less than 2.5 mm; or less than 1 mm. For example, the predetermined distance may be between 0.5 mm and 2.5 mm, such as between 1 mm and 2 mm, for example about 1.5 mm.

Balancing the distance by which the cutting edge extends against the distance by which it retracts, produces a compact bespoke piercing tool that is perfectly suited to its purpose of cutting an aperture into the covering layer of one-piece wound dressing, so as to change its configuration from being (only) suitable and intended for use without a pressure gradient wound treatment system, to being (only) suitable and intended for use in a pressure gradient wound treatment system.

Figure 3:
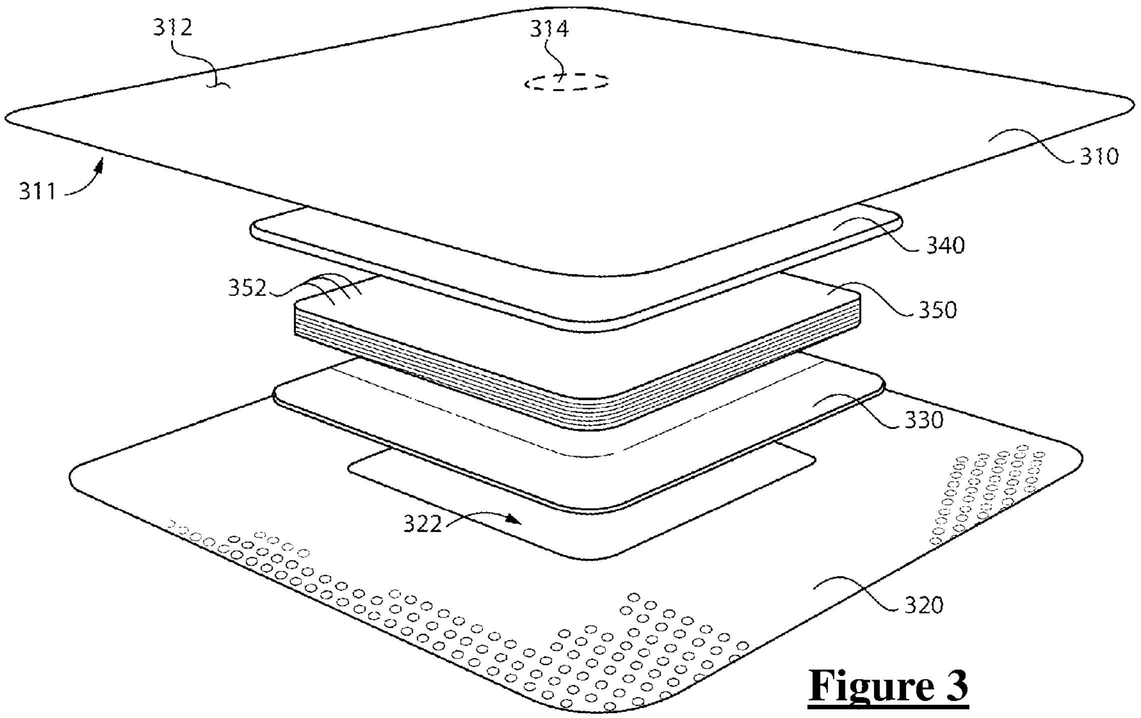
FIG. 3 is an exploded view of another embodiment of a wound dressing configured for use without a wound therapy apparatus.

With additional reference to FIGS. 3-4, illustrated therein is a schematic of another exemplary wound dressing 300 that can be selectively configured for use in a pressure gradient wound treatment system, using the piercing tool 20.

The illustrated wound dressing 300 generally includes a covering layer 310 and an adhesive layer 320 for adhering the wound dressing 300 adjacent the wound. In certain embodiments, the wound dressing 300 further comprises a wound contact layer 330 for contacting the wound, a pressure dispersion layer 340, a plurality of absorbent material layers 350 disposed between the wound contact layer 330 and the pressure dispersion layer 340.

The covering layer 310 has a first surface 311 and a second surface 312, and the first surface 311 is adjacent, and in contact with, the pressure dispersion layer 340 and the adhesive layer 320. The covering layer 310 defines a cavity in which the pressure dispersion layer 340 is arranged. In certain embodiments, the covering layer 310 is formed of a polyurethane film. The covering layer 310 comprises indicia 314 again in the form of a dashed circle, arranged in the optimal position for connection to a source of negative pressure.

The polyurethane film is transparent, so the indicia can be printed on the inside first surface 311 or the outside, second, surface 312 of the film layer 310.

The adhesive layer 320 generally defines a border about an opening 322 for receiving the wound. In certain embodiments, the adhesive layer 320 comprises a silicone adhesive. In certain embodiments, the adhesive layer 320 may be perforated.

The wound contact layer 330 overlaps the border defined by the adhesive layer 320, and is configured to contact the wound via the opening 322. In certain embodiments, the wound contact layer 330 may comprise Medicel™. In certain embodiments, the wound contact layer 330 comprises carboxymethylated cellulose fibers. In certain embodiments, the wound contact layer 330 may comprise HYDROFIBER®. In certain embodiments, the wound contact layer 330 may be reinforced, for example via nylon stitching. Thus, the wound contact layer 330 may comprise reinforcing nylon stitching 332.

The pressure dispersion layer 340 is adjacent and in contact with the first surface 311 of the cover layer 310. In certain embodiments, the pressure dispersion layer 340 may be provided as a polyester foam layer. In certain embodiments, the pressure dispersion layer 340 comprises reticulated foam.

The absorbent material layers 350 are positioned between the wound contact layer 330 and the pressure dispersion layer 340. The wound dressing 300 may, for example, comprise eight absorbent material layers 350. In certain embodiments, one or more of the absorbent material layers 350 may comprise carboxymethylated cellulose fibers. In certain embodiments, one or more of the absorbent material layers 350 may comprise Medicel™. In certain embodiments, one or more of the absorbent material layers 350 may comprise HYDROFIBER®. In certain embodiments, one or more of the absorbent material layers 350 further comprises fenestrations 352.

Figure 5:
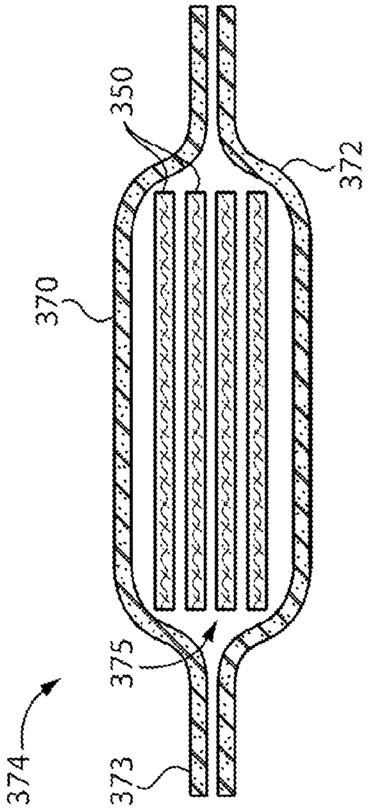
FIG. 5 is a cross-sectional view of a portion of the wound dressing illustrated in FIG. 3.

In certain embodiments, as shown in FIG. 4, the wound dressing 300 may include an additional layer 370 between the pressure dispersion layer 330 and the uppermost absorbent layer 350. The additional layer 370 may, for example, be formed of thermoplastic. In certain embodiments, the additional layer 370 may be provided as a thermoplastic spun lace layer. In certain embodiments, the wound dressing 300 may further comprise a nonwoven spun lace layer 372 connected to the wound contact layer 330. In certain embodiments, an envelope structure 374 is formed by joining peripheral portions 373 of the thermoplastic spun lace layer 370 and the nonwoven spun lace layer 372 such that the plurality of absorbent material layers 350 are disposed substantially within an interior cavity 375 of the envelope structure 374, for example as illustrated in FIG. 5. In certain embodiments, the absorbent material layers 350 are disposed within the interior cavity 375 of the envelope structure 374.

In certain embodiments, the wound dressing 300 may include a further layer 380 positioned between the wound contact layer 330 and the lowermost absorbent layer 350. The further layer 380 may, for example, be a polyester/viscose layer.

As is well known, and therefore not shown, the wound dressing 300 may be provided with a removable release layer on the underside, covering the adhesive layer 320 and the underside of the wound contact layer 330; and it may be individually packaged within a sterile package.

As illustrated in FIGS. 3-5, the wound dressing is configured for use without a pressure gradient wound therapy system. To use the wound dressing 300 without a pressure gradient wound therapy system, it is simply removed from its sterile packaging, then the release layer is simply removed and the dressing applied in the same way as an ordinary wound dressing. Again, it will be noted that in this configuration the entire region of the covering layer 310 within the peripheral adhesive border defined by the layer 320 is uninterrupted and closed, sealing the wound against microbes/bacteria that could cause infection.

FIG. 6 shows the wound dressing 1 of FIGS. 3-5 configured for use with a pressure gradient wound therapy system. Here, a user has cut through the cover layer 310 using the piercing tool 20. To cut through the covering layer 310, the user arranges the base of the housing 23 on the covering layer 310 of the dressing 300 in the region of the indicia 314. In this embodiment, the base of the housing 23 and the indica 314 have the same circular shape and size, so the user can align the piercing tool 20 in the optimal position on the dressing 300.

The user then presses down on the upper surface of the button 25. This causes the support to move downward, against the bias of the spring 27, extending the cutting edge 21 out of the base of the housing 23 to cut into the covering layer. Continued pressing brings the lip 26 of the button 25 into abutment with the upper surface of the flange 24, preventing the cutting edge from extending more than a predetermined distance out of the base of the housing. This ensures that the cutting edge extends right through the covering layer 310 and slightly into the pressure distribution layer 340, but not into the layers beneath.

The button 25 is then released and the compression spring 27 returns, biasing the actuator back to the rest position, with the cutting edge in a retracted position. The tool 20 can then be removed from the dressing and might carry with it a circular chad cut from the covering layer 310. Typically however, the chad will remain in the aperture and can be peeled out by a user to leave an aperture as shown in FIG. 6.

As such, the region of the covering layer 310 within the peripheral adhesive border defined by the layer 320 is now interrupted by the aperture 306, which forms an opening.

Next, and as shown in FIGS. 8 and 9, a port 307 is adhered to the outside, second surface 312 of the cover layer 310. An adhesive ring 366 attaches the port 307 to form a seal between one end 361 of the tube 360 and the port 307. The opposite end 362 of the tube 360 may be connected with a fitting such as a Luer lock 364.

With additional reference to FIG. 10, illustrated therein is a pressure gradient wound therapy system 400 according to certain embodiments. The pressure gradient wound therapy system 400 comprises a pump 410 for generating negative pressure, a wound dressing 420 (which may be the wound dressing 1 or 300 described above) for covering and protecting a wound, an inline filter 430, a first pressure tube 440 having a first interior lumen 442, a second pressure tube 450 having a second interior lumen 452, and a flexible connector 460. The first pressure tube 440 is disposed between the pump 410 and the inline filter 430. The second pressure tube 450 is disposed between the inline filter 430 and the flexible connector (or port) 460. The flexible connector 460 is disposed between the second pressure tube 450 and the wound dressing 420 such that the pump 410 and the wound dressing 420 are in fluid communication via the interior lumens 442, 452.

The piercing tool is preferably provided in a kit and most preferably arranged in the kit within a sterile package. As illustrated schematically in FIG. 11, the kits can comprise a piercing tool 20 within a sterile package 28 and at least one of the following items, all of which are included in this exemplary kit:

(a) packaging 500 indicating that the piercing tool is configured to pierce a covering layer of a wound dressing to produce an aperture therein and thereby configure the wound dressing for use in a pressure gradient wound therapy. In this example the packaging is a cardboard box, printed with instructions for use.

(b) instructions instructing a user as to how to use the piecing tool to configure a wound dressing for use in a pressure gradient wound therapy system. In this example, the instructions are printed on a leaflet 502 included in the box.

(c) one or more selectively configurable wound dressings 1, 300, 420, the wound dressings 1, 300, 420 being configurable for use in a pressure gradient wound therapy system and without a pressure gradient wound therapy system. In this embodiment, a plurality of such wound dressings 1, 300, 420 are provided, each in individual sterile packages.

(d) a source of non-atmospheric pressure. In this embodiment, the source of non-atmospheric pressure is the pump 410.

(e) a port for connection to the covering layer of the wound dressing to connect the wound dressing to a source of non-atmospheric pressure. In this embodiment the port is the port 307 described above.

(f) tubing for connection between a wound dressing and a source of non-atmospheric pressure. In this embodiment tubing 440 described above is included.

For use where it is envisioned that a wound will initially require treatment with a pressure gradient wound therapy system, the kit may comprise a piercing tool 20 and one or more of items d, e and f, for example all of items, d, e and f, and optionally items a and/or b and/or c as well. As such, the user can be provided with all the equipment required to use the wound dressings 1/300/420 with a pressure gradient wound therapy system.

In order to use such a kit, the user (e.g. a patient or HCP) can cut an aperture in a dressing 1/30/420, optionally in the region of indica, using the piercing tool 20; attach a port 307 thereto, around the aperture, and in fluid communication therewith; attach one end of the tubing 440 to the port 307 and the other to the pump 410 and run the pump 440 to provide non-atmospheric (e.g. negative) pressure to the wound.

Then, if/when the pressure gradient therapy is no longer necessary, the user can use up any remaining wound dressings 1/300/420 without the pressure gradient wound therapy system, by applying them to the wound without cutting an aperture in the dressings 1/300/420, so as to maintain a sealed environment around the wound.

On the other hand, for use where it is envisioned that a wound does not initially require treatment with a pressure gradient wound therapy system (and most preferably where it is envisioned that a wound does not require treatment with a pressure gradient wound therapy system, but it is considered that there is a risk that the wound will not heal well without a pressure gradient so in future, pressure gradient wound therapy might be useful), the kit may comprise the piercing tool 20, one or preferably a plurality of the dressings of item c, and preferably one or both of items a and b. As such, the user has the dressings which can be used without a pressure gradient wound therapy system and can simply apply a dressing 1/300/420 to the wound in the configuration for use without a pressure gradient wound therapy system. Thus the user simply remove the release layer and apply the dressing to the wound without cutting an aperture in the region of the indicia 2, 314, so that the cover layer is uninterrupted and closed within the adhesive border, and the is wound sealed against bacteria/microbes.

Then, should it be determined that the wound would benefit from pressure gradient therapy (e.g. negative pressure), the user can follow the instructions from the packaging/instructions (where included), and cut a hole in the covering layer 3/310 in the region of the indicia 2/314 using the piercing tool 20 and apply a pressure gradient wound therapy system as outlined above (sourced for example from another kit), without having to first remove the dressing 1/300/420 (which can present an opportunity for infection).

For use where it is determined after the event that a piercing tool and one or more of items d, e and f, for example all of items, d, e and f, and optionally items a and/or b and/or c as well would be useful. As such, the user can be provided with all the equipment required to convert a wound dressing 1/300/420 in-situ for use with a pressure gradient wound therapy system.

In order to use such a kit, the user (e.g. a patient or HCP) can cut an aperture in a dressing 1/30/420, optionally in the region of indica, using the piercing tool 20; attach a port 307 thereto, around the aperture, and in fluid communication therewith; attach one end of the tubing 440 to the port 307 and the other to the pump 410 and run the pump 440 to provide non-atmospheric (e.g. negative) pressure to the wound.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Each of the documents referred to above is incorporated herein by reference. Except in Examples, or where otherwise explicitly indicated, all numerical quantities in this description specifying amounts of materials, device dimension, and the like, are to be understood as modified by the word "about."

Unless otherwise indicated, each chemical or composition referred to herein should be interpreted as being a commercial grade material which may contain the isomers, byproducts, derivatives, and other such materials which are normally understood to be present in the commercial grade.

The one or more embodiments are described above by way of example only. Many variations are possible without departing from the scope of protection afforded by the appended claims.

The invention claimed is:

1. A packaged kit of parts for use with a selectively configurable one-piece wound dressing, the one-piece wound dressing being configurable for use in a pressure gradient wound therapy system and without the pressure gradient wound therapy system; the kit comprising:

a piercing tool configured to pierce a covering layer of the one-piece wound dressing to produce an aperture therein and thereby configure the one-piece wound dressing for use in the pressure gradient wound therapy system;

one or more of the one-piece wound dressing configurable for use in the pressure gradient wound therapy system and without the pressure gradient wound therapy system, the one-piece wound dressing comprising a wound dressing cavity integrated with a covering layer, the wound dressing cavity containing therein a pressure distribution layer, one or more absorbent layers, and a wound contact layer;

instructions instructing a user as to how to use the piecing tool to configure the one-piece wound dressing for use in the pressure gradient wound therapy system; and a sealed package comprising therein the one or more of the one-piece wound dressing, the piercing tool, the instructions and at least one of:

a) packaging indicating that the piercing tool is configured to pierce a covering layer of the one-piece wound dressing to produce an aperture therein and thereby configure the one-piece wound dressing for use in the pressure gradient wound therapy system;

(b) a source of non-atmospheric pressure;

(c) a port for connection to the aperture in the covering layer to connect the one-piece wound dressing to the source of non-atmospheric pressure; or (d) tubing for connection between the one-piece wound dressing and the source of non-atmospheric pressure, wherein the piercing tool comprises a cutting edge and a housing, the cutting edge being retractable into the housing, and wherein the instructions instructing a user as to how to use the piercing tool to configure the one-piece wound dressing for use in the pressure gradient wound therapy system comprise instructions regarding cutting through the covering layer but not through the cavity to create the aperture to provide fluid communication between the wound dressing cavity and a source of non-atmospheric pressure.

2. A packaged kit of parts according to claim 1 wherein the piercing tool is provided in a sterile package.

3. A packaged kit of parts according to claim 1 or 2 wherein the piercing tool has a curved cutting edge.

4. A packaged kit of parts according to claim 3 wherein the piercing tool has a circular cutting edge.

5. A packaged kit of parts according to claim 1 wherein the housing is a tubular housing; the cutting edge being retractable into the tubular housing.

6. A packaged kit of parts according to claim 5 wherein the piercing tool comprises an actuator, wherein actuation of the actuator moves the cutting edge to an extended position.

7. A packaged kit of parts according to any of claims 5 to 6 wherein the cutting edge is biased towards a retracted position.

8. A packaged kit of parts according to claim 7 wherein the bias is a spring-bias.

9. A packaged kit of parts according to claim 6 wherein the cutting edge is arranged to extend a predetermined extended distance from the housing in the extended position.

10. A packaged kit of parts according to claim 9 wherein the predetermined extended distance is greater than 0.5 mm.

11. A packaged kit of parts according to claim 9 wherein the predetermined extended distance is less than 2.5 mm.

12. A packaged kit of parts according to claim 1 wherein the cutting edge is arranged to retract a predetermined retracted distance into the housing in the retracted position.

13. A packaged kit of parts according to claim 12 wherein the predetermined retracted distance is between 5 mm and 10 mm.

14. A packaged kit of parts according to claim 1 wherein the cutting edge is extendable from one end of the housing and an actuator is arranged at the opposite end of the housing, wherein the actuator moves the cutting edge to an extended position.

15. A packaged kit of parts according to claim 1 wherein the housing comprises an inwardly extending flange which acts as a guide for guiding the cutting edge.

16. A packaged kit of parts according to claim 15, wherein the flange supports a biasing spring for providing a spring bias.

17. A packaged kit of parts according to claim 6, wherein the actuator comprises a support extending from a button.

18. A packaged kit of parts according to claim 17 wherein the housing comprises an inwardly extending flange which acts as a guide for guiding the cutting edge, wherein an outer peripheral surface of the support is guided by an inner edge of the flange and an outer peripheral surface of the button is guided by an inner tubular surface of the housing.

19. A packaged kit of parts according to claim 1 including at least a) packaging indicating that the piercing tool is configured to pierce the covering layer of the one-piece wound dressing to produce the aperture therein and thereby configure the one-piece wound dressing for use in the pressure gradient wound therapy system.

20. A packaged kit of parts according to claim 1 including at least (b) the source of non-atmospheric pressure.

21. A packaged kit of parts according to claim 1 including at least (c) the port for connection to the covering layer of the wound dressing to connect the one-piece wound dressing to the source of non-atmospheric pressure; the kit being arranged within the sealed package and the piercing tool being independent of the port.

22. A packaged kit of parts according to claim 1 including at least (d) tubing for connection between the one-piece wound dressing and the source of non-atmospheric pressure.

23. A packaged kit of parts according to claim 1 wherein the covering layer comprises a first surface facing the pressure distribution layer, the one or more absorbent layers, and the wound contact layer and defining the one-piece wound dressing cavity, and a second surface; wherein the second surface of the covering layer comprises an indica, the indica denoting a suitable position in the covering layer to create the aperture to provide fluid communication between the wound dressing cavity and the source of non-atmospheric pressure; wherein the shape and/or size of the indicia matches the shape and/or size of the piercing tool.

* * * * *